United States Patent [19]

Wilson, Jr. et al.

[11] Patent Number: 5,133,724
[45] Date of Patent: Jul. 28, 1992

[54] ABDOMINAL AORTIC CLAMP

[75] Inventors: Robert W. Wilson, Jr., Dresher; William H. Pilling, North Wales, both of Pa.

[73] Assignee: Pilling Co., Fort Washington, Pa.

[21] Appl. No.: 680,394

[22] Filed: Apr. 4, 1991

[51] Int. Cl.$^5$ ............................................ A61B 17/00
[52] U.S. Cl. .................................. 606/151; 606/208; 606/207
[58] Field of Search ............... 606/151, 205, 206, 207, 606/208

[56] References Cited

U.S. PATENT DOCUMENTS

| | | | |
|---|---|---|---|
| 614,854 | 11/1898 | Frank et al. | 606/207 |
| 1,659,112 | 2/1928 | Littlejohn | 606/208 |
| 3,866,610 | 2/1975 | Kletschka | 606/208 |
| 3,952,749 | 4/1976 | Fridolph et al. | 606/208 |
| 4,655,223 | 4/1987 | Kim | 606/207 |

Primary Examiner—Stephen C. Pellegrino
Assistant Examiner—Gary Jackson
Attorney, Agent, or Firm—Howson & Howson

[57] ABSTRACT

A vascular clamp for temporary occlusion in the infrarenal region of the abdominal aorta during performance of surgery associated with abdominal aneurysms. Pivoted handles are operatively connected to respective one ends of relatively slidable elongate members, and parallel jaws laterally extend from the other ends. Manipulating the handles in scissors-like motion causes the jaws to translate between open and close positions. A ratchet-and-tooth arrangement interengages the handles as the jaws close.

14 Claims, 2 Drawing Sheets

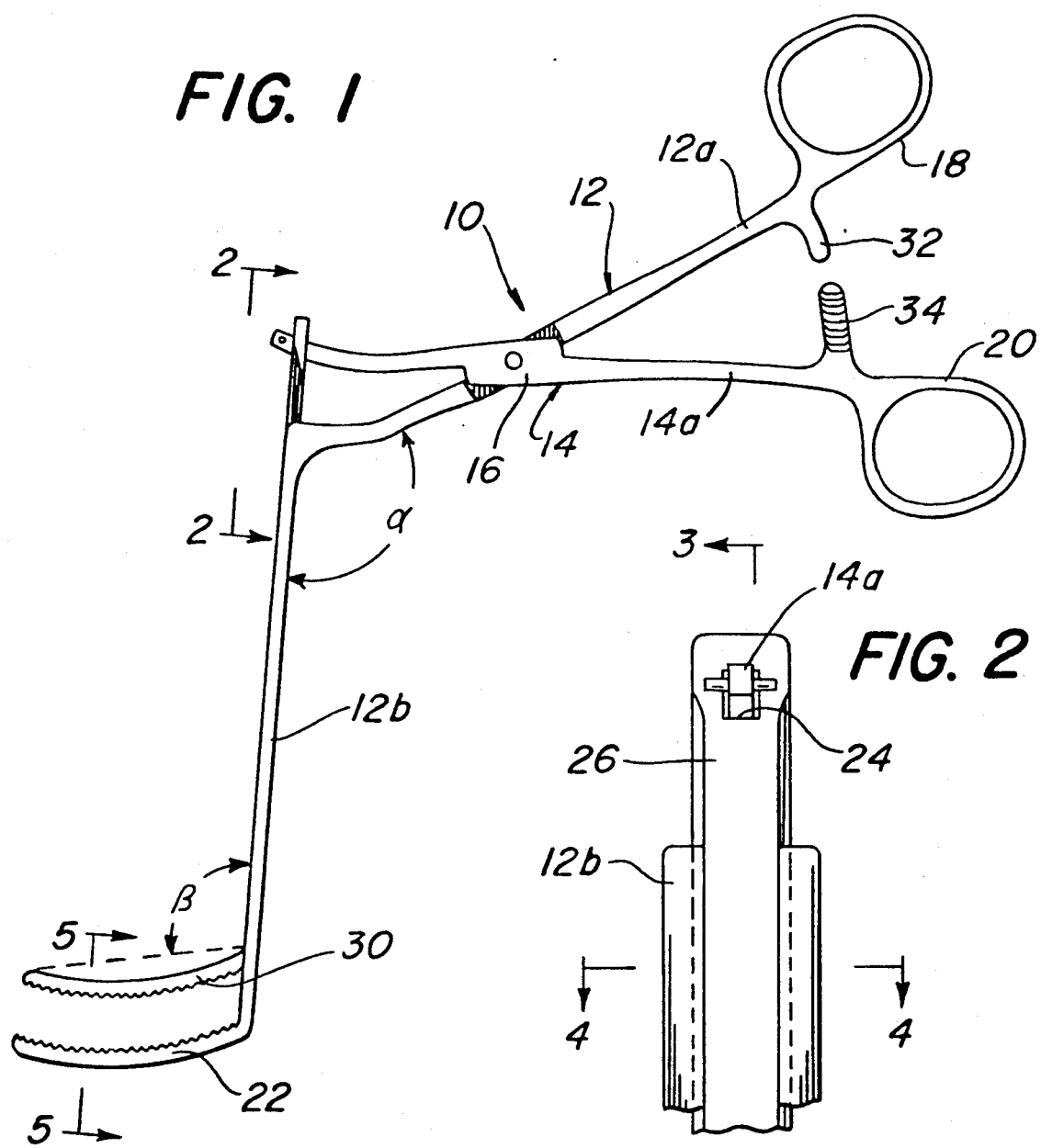

ABDOMINAL AORTIC CLAMP

BACKGROUND OF THE INVENTION

The present invention relates generally to surgical instruments for occluding blood vessels during surgical procedures, and more particularly to a vascular clamp suitable for temporary occlusion of the abdominal aorta during surgical procedures such as in the treatment of abdominal aneurysms.

Forceps, hemostats and clamps for temporary occlusion of blood vessels come in a myriad of sizes and configurations to meet the unique requirements of many surgical procedures as well as to satisfy the individual preferences of surgeons. For instance, the length and curvature of the clamp should enable convenient manipulation and compression of the jaws at a precise location and orientation without the handles obstructing the operating site after they have been locked in place. This is especially important for surgical procedures, such as aneurysmectomies, aneurysmoplasties or iliac bypasses, where the clamp must reach to the infrarenal region of the abdominal aorta. Among the preferred and more versatile clamps for these procedures are the DeBakey and Grant clamps manufactured by Pilling Company of Fort Washington, Pa. For instance, the DeBakey curved aneurysm clamp compresses the aorta from side-to-side with the handles extending upward in the abdominal wound after the clamp is locked in place. In addition to obstructing the surgeon's access, only an anterior edge of the compressed aorta is completely exposed making it more difficult in some cases to suture a graft close to the clamp. Furthermore, there is a greater risk of dislodging atherosclerotic matter because the jaws pinch the posterior wall of the aorta where such matter first tends to build up. Other aortic clamps of DeBakey and Grant, are useful in other cases for temporary occlusion of the abdominal aorta during performance of resection and graft replacement. The gripping faces of the jaws are flat or curved upward to permit the aorta to be clamped with minimal distortion and trauma. The jaws are also specially angled in parallel alignment with the pivot axis of the handles to permit anterior-to-posterior clamping of the aorta. However, it is not always possible for the handles to remain stabilized in the abdominal wound after they are clamped in place. Rather they tend to move, causing the jaws to twist or distend the aortic walls and dislodge any atheromatous matter which may be present on the posterior wall.

The clamps described above are not well-suited for anterior-to-posterior closure of the abdominal aorta where adjacent viscera may interfere with the manipulation and stability of the clamp after the jaws have been locked in place.

SUMMARY OF THE INVENTION

Accordingly, it is an object of the present invention to provide an improved vascular clamp suitable for temporarily occluding the aorta during the performance of aortic surgery.

Further objects of the invention are to provide a vascular clamp for temporary occlusion in the infrarenal region of the abdominal aorta during the performance of surgery on abdominal aneurysms, which facilitates anterior-to-posterior clamping of the aorta; to minimize distortion and trauma of the wall of the aorta between the jaws of the clamp; to afford the surgeon unobstructed visibility and access to the operating region; and to place the anterior and posterior walls in a preferred aspect for grafting and suturing purposes.

Briefly, these and other objects of the invention are accomplished with a vascular clamp having parallel, arcuate jaws translatable between open and close positions by offset, pivotally connected handles. The jaws extend laterally from adjacent ends of two elongate members slidable lengthwise relative to each other, the other ends of the members being operatively connected to the handles. Manipulating the handles in scissors-like fashion causes the jaws to open and close. A ratchet-and-tooth arrangement interengages the handles as the jaws close. Lengthwise rows of serrated teeth in the opposed surfaces of the jaws prevent slippage and minimize trauma at the clamp site.

Other objects and novel features of the invention will become more apparent from the following detailed description when considered in conjunction with the accompanying drawings.

BRIEF DESCRIPTION OF THE DRAWINGS

FIG. 1 is an elevational view of a vascular clamp constructed according to the invention suitable for temporary occlusion of the abdominal aorta during surgery;

FIG. 2 is a frontal view of a portion of the clamp taken on plane 2—2 of FIG. 1;

FIG. 3 is a longitudinal view in cross section of a portion of the clamp taken on plane 3—3 of FIG. 2;

DESCRIPTION OF THE PREFERRED EMBODIMENT

Figure 4:
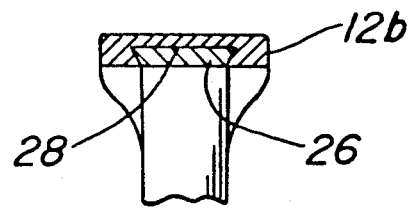
FIG. 4 is a transverse cross section of the clamp taken on plane 4—4 of FIG. 2.

Referring now to the drawings wherein like characters designate like or corresponding parts throughout the several views, there is shown in FIG. 1 a vascular clamp 10 suitable for temporary occlusion of the abdominal aorta during surgery involving the infrarenal region of the aorta. A pair of handles 12 and 14, preferably of steel such as type 410X martensitic stainless steel, are pivotally connected together by a stress-free hinge integrally formed in a box lock joint 16 such as disclosed in U.S. Pat. No. 3,952,749 to John Fridolph et al. Handles 12 and 14 include straight-sections 12a and 14a manipulated in scissors-like motion by finger loops 18 and 20 formed at proximal ends of the handles. The distal end of handle 12, opposite from loop 18, further includes another straight section 12b which rigidly extends downward from section 12a to form an angle α therewith of approximately 120° and which terminates at a lower arcuate jaw 22. As shown in FIGS. 2 and 3, the distal end of handle section 14a, opposite from loop 20, slidably extends through an aperture 24 in one end of a stem 26. As shown in FIG. 4, stem 26 slides in a dovetail-like groove 28 formed along the entire length of handle section 12b. Stem 26 terminates at an upper arcuate jaw 30 parallel to lower jaw 22 as shown in FIG. 1. The lengths of section 12b and stem 26 are sufficient to enable jaws 22 and 30 to reach the aorta with handles 12 and 14 extending laterally over the retracted wall of an abdominal wound abreast of the clamping site. For a normal size subject, a length of 17 cm. has been found to be satisfactory. The size of aperture 24 is sufficient to allow handle 12 to pivot freely in handle 14 over the full range of relative translation of jaws 22 and 30.

Figure 5:
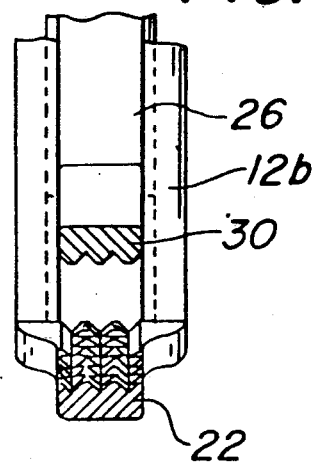
FIG. 5 is a transverse cross section of jaws of the clamp taken on plane 5—5 of FIG. 1.

Jaws 22 and 30 extend forward approximately 4 cm. from section 12b or stem 30 respectively, on a spoon-like arc about 3 mm. in depth on chords drawn between the ends. The chords form with section 12b an angle $\beta$ of approximately 100°. This configuration has been found especially convenient for placing jaw 22 in the space underneath the abdominal aorta and for fully clamping the aorta with minimal distortion of the posterior wall. As shown in FIG. 5, jaw 22 has four arcuate rows of serrated teeth 22a opposed by three arcuate rows of serrated teeth 30a in jaw 30, the coarseness being selected to prevent slippage of tissue and to minimize trauma at the clamp site. For details of a typical atraumatic clamping jaw structure, reference may be made to U.S. Pat. No. 3,608,554, dated Sep. 28, 1971.

Referring once again to FIG. 1, locking lugs 32 and 34, extending from arms 12 and 14 adjacent to finger grips 18 and 20, define a ratchet-and-tooth arrangement for interengaging the handles when jaws 22 and 24 are squeezed toward closing. The bending resilience of handles 12 and 14 determines the clamping force at the jaws.

Figure 6:
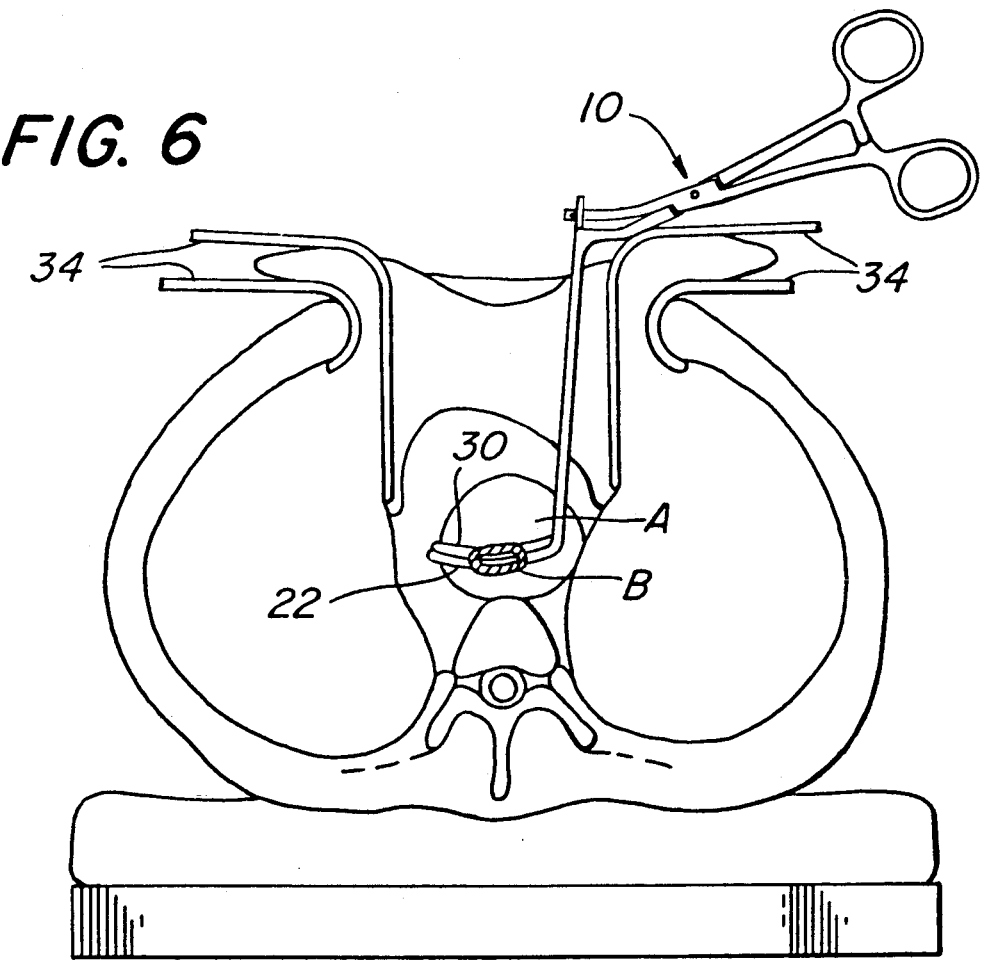
FIG. 6 is a schematic inferior view of a transverse section of a supine patient, taken at an abdominal exposure, with the clamp of FIG. 1 applied to the descending aorta above an aneurysm.

The manner in which clamp 10 may be utilized in a surgical procedure such as an aneurysmectomy is illustrated in FIG. 6 in which the abdominal wall and viscera of a supine patient are displaced laterally by retractors 34 to expose an abdominal aneurysm A. Jaws 22 and 30 are shown clamped to the infrarenal region of aorta B approximately one cm. above the aneurysm. This position was achieved by inserting jaw 22 underneath the aorta A in a substantially horizontal motion, and then manipulating handles 12 and 14 for anterior-to-posterior clamping between both jaws. Posterior wall distortion and risk of dislodging any atherosclerotic debris are minimized. After the jaws are locked by lugs 32 and 34, handles 12 and 14 will extend laterally out of the way of the surgical region with substantially no strain or twist on the aorta.

Alternative means for connecting the handles to translate jaws 22 and 30 are contemplated which will achieve similar results. For instance, the rigid and slidable connections of handles 12a and 14a may be interchanged on section 12b and stem 26, or they may both be pivotally connected to section 12b and stem 26.

Some of the many advantages and novel features of the invention should now be readily apparent. For example, a vascular clamp is provided which is particularly suitable for temporary occlusion of the descending aorta during surgical treatment of abdominal aneurysms. The jaws may be readily manipulated into a clamping position to provide optimum exposure to the aorta for suturing and grafting purposes. Complete anterior-to-posterior clamping minimizes the risk of disturbing atheromatous matter which may accumulate on the posterior wall of the aorta; and after the jaws are locked in a clamped position, the handles remain in a stabilized position out of the way of the surgical site.

Various changes in the details, steps, and arrangement of parts, which have been herein described and illustrated to explain the nature of the invention, may be made by those skilled in the art within the principle and scope of the invention as expressed in the appended claims.

I claim:

1. A vascular clamp suitable for temporary occlusion of the abdominal aorta, comprising, in combination:
   first and second elongate rigid members slidable lengthwise relative to each other;
   first and second jaws parallel to each other and laterally extending respectively from adjacent one ends of said members and movable in a plane between open and closed positions; and
   first and second handles pivotally connected and extending laterally from respective adjacent other ends of said members in a direction opposite of said jaws for manipulating said jaws in said plane.

2. A vascular clamp according to claim 1 wherein:
   said jaws form spoon-like arcs for minimizing distortion of the posterior wall of the aorta when clamped therebetween.

3. A vascular clamp according to claim 2 wherein:
   a chord drawn between the ends of each of said jaws forms with said members an angle of approximately 100 degrees in the pivotal plane of said handles.

4. A vascular clamp according to claim 1 wherein:
   said first and second jaws each include a plurality of rows of serrated teeth aligned along the length of said jaws.

5. A vascular clamp, comprising, in combination:
   first and second elongate handles pivotally connected to each other and defining proximal ends having finger grips for manipulation in a single plane in scissors-like motion;
   first and second elongate rigid members, one end of each extending laterally from the distal end of respective ones of said handles and slidable lengthwise relative to each other; and
   first and second jaws parallel to each other and extending laterally from respective other ends of said members in a direction opposite of said handles and movable in opposition to each other in said plane.

6. A vascular clamp according to claim 5 wherein:
   said jaws arch upward.

7. A vascular clamp according to claim 6 wherein:
   a chord drawn between the ends of each of said jaws forms with said members an angle of approximately 100 degrees in the pivotal plane of said handles.

8. A vascular clamp according to claim 5 wherein:
   said first and second jaws each include a plurality of rows of serrated teeth aligned along the length of said jaws.

9. A vascular clamp suitable for temporary occlusion of the abdominal aorta, comprising, in combination:
   first and second elongate rigid members, said first member slidable in a track formed along the length of said second member;
   first and second jaws parallel to each other and laterally extending respectively from adjacent one ends of said members and formed to grip opposite walls of the aorta;
   pivotally connected first and second handles defining proximal ends with finger grips, and distal ends operatively connected respectively to adjacent other ends of said first and second members for manipulating said jaws between open and closed positions; and said other end of said first member includes an aperture slidably receiving the distal end of said second handle, and said other end of said second member is rigidly connected to the distal end of said second handle.

10. A vascular clamp according to claim 9 wherein: said second member forms with said second handle an angle of approximately 120 degrees in the pivotal plane of said handles.

11. A vascular clamp according to claim 9 further comprising:
locking means extending from said handles for maintaining said jaws compressed about the aorta.

12. A vascular clamp, comprising, in combination:
first and second elongate handles pivotally connected to each other, defining proximal ends having finger grips for manipulation in scissors-like motion;
first and second elongate rigid members, each operatively connected at one end to the distal end of one of said handles, said first member slidable in a track formed along the length of said second member, said one end of said first member includes an aperture slidably receiving the distal end of said first handle, and said one end of said second member is rigidly connected to the distal end of said second handle; and
first and second jaws parallel to each other, each extending laterally from another end of a respective one of said members opposite its said one end.

13. A vascular clamp according to claim 12 wherein: said second member forms with said second handle an angle of approximately 120 degrees in the pivotal plane of said handles.

14. A vascular clamp according to claim 12 further comprising:
locking means extending from said handles for maintaining said jaws compressed about the aorta.

* * * * *